(12) United States Patent
Lilienthal et al.

(10) Patent No.: US 6,675,664 B1
(45) Date of Patent: Jan. 13, 2004

(54) BACK FLUSHABLE SAMPLE PROBE

(75) Inventors: Scott Edward Lilienthal, Laurel, MD (US); James Barden, Chester, MD (US)

(73) Assignee: ITT Manufacuring Enterprises, Inc., Wilmington, DE (US)

( * ) Notice: Subject to any disclaimer, the term of this patent is extended or adjusted under 35 U.S.C. 154(b) by 211 days.

(21) Appl. No.: 10/013,842

(22) Filed: Dec. 13, 2001

(51) Int. Cl.[7] .................................................. G01N 1/00
(52) U.S. Cl. ................................ 73/863.23; 73/863.24; 210/122
(58) Field of Search ......................... 73/863.23, 863.24, 73/863.81–863.83, 863.85, 864.34, 864.35, 803.23; 210/348, 354, 357, 391, 393, 416.1, 435, 443, 446, 122; 96/413

(56) References Cited

U.S. PATENT DOCUMENTS

| | | | |
|---|---|---|---|
| 1,993,175 A | | 3/1935 | Libbey et al. |
| 2,052,013 A | * | 8/1936 | Beghetti |
| 2,731,299 A | * | 1/1956 | Bramming |
| 3,039,309 A | * | 6/1962 | Vesper et al. ............ 73/863.24 |
| 3,184,973 A | * | 5/1965 | Bradley .................... 73/863.24 |
| 3,966,606 A | | 6/1976 | Ahmad |
| 4,094,187 A | * | 6/1978 | Navarre, Jr. ............. 73/863.83 |
| 5,039,322 A | * | 8/1991 | Holzl ....................... 73/863.24 |
| 5,584,314 A | | 12/1996 | Bron |
| 5,707,527 A | | 1/1998 | Knutson et al. |
| 5,777,241 A | * | 7/1998 | Evenson .................. 73/863.24 |
| 5,961,700 A | | 10/1999 | Oliver |

\* cited by examiner

*Primary Examiner*—Robert Raevis
(74) *Attorney, Agent, or Firm*—Edell, Shapiro & Finnan

(57) ABSTRACT

A back flushable sample probe includes a hollow fitting securable to a fluid supply source and a strainer assembly disposed within the fitting. The strainer assembly includes a movable first member and a second member secured within the fitting. The first member is movable to contact the second member and form a strainer at the engaging surface between, the first and second members, where the strainer permits a fluid sample to flow through the engaging surface but prevents debris entrained in the fluid to pass therethrough. During back flushing of the sample probe, the first member disengages from the second member, causing any debris accumulated at the engaging interface to be removed from the sample probe.

26 Claims, 5 Drawing Sheets

BACK FLUSHABLE SAMPLE PROBE

BACKGROUND OF THE INVENTION

1. Field of the Invention

The present invention relates to a sample probe for extracting a fluid sample from a fluid supply source and, in particular, a back flushable sample probe which can be readily freed of debris by flushing fluid through the probe in a reverse direction.

2. Description of the Related Art

Sampling devices for removing a fluid sample from a source of flowing fluid, e.g., a pipe or conduit, may require filtering or straining of heterogeneous material from the fluid sample to create a homogeneous yet representative sample prior to collection and analysis. Many conventional sampling devices employ a mesh type strainer or similar porous medium to remove debris from fluid to be collected and sampled. In certain fluid processing systems, such as municipal wastewater sewage treatment systems and storm sewer systems, the fluid to be sampled contains debris of significantly varying sizes. In such systems, the filter or strainer can become clogged very quickly, leading to an increase in pressure at the strainer and an inability to obtain a fluid sample passing through the strainer. Strainer devices for such systems may employ a back flushing mechanism to remove material sticking to the strainer. However, even back flushing is ineffective in situations where material becomes severely lodged or jammed within the holes or apertures of the strainer. In those situations, the sample device must be disengaged and brought offline from the fluid supply source so that the strainer may be removed and physically and/or chemically treated to dislodge material plugging the apertures of the strainer.

A sampling device including a strainer is therefore desirable that can effectively remove varying types of debris from a fluid sample and that can readily dislodge material stuck within the apertures of the strainer without the need to disengage the device from a fluid supply source.

SUMMARY OF THE INVENTION

Therefore, in light of the above, and for other reasons that become apparent when the invention is fully described, an object of the present invention is to provide a fluid sample probe securable to a fluid supply source that effectively filters or strains a fluid sample from the fluid supply source and delivers the fluid to a fluid collection site.

Another object of the present invention is to provide a back flushing feature within the sample probe that effectively dislodges any material that may become stuck within the strainer of the sample probe.

A further object of the present invention is to effectively dislodge material stuck within the sample probe without requiring disengaging of the sample probe from the fluid supply source.

The aforesaid objects are achieved individually and in combination, and it is not intended that the present invention be construed as requiring two or more of the objects to be combined unless expressly required by the claims attached hereto.

In accordance with the present invention, a back flushable sample probe is provided to filter or strain a fluid sample from a fluid supply source, such as a fluid conduit, for delivery to a fluid sample collector. The sample probe includes a fitting to withdraw the fluid sample from the fluid supply source for delivery to a sample collector and a strainer assembly disposed within the fitting and including a first member and a second member. The first member moves within the fitting to releasably engage with the second member which is secured and immobilized within the fitting. A strainer is formed and becomes operable to effectively remove debris from the fluid sample upon engagement of the first member with the second member. Back flushing is also easily accomplished by reversing the direction of fluid flow within the fitting to force fluid from the fitting back into the fluid supply source. Back flushing of fluid in the sample probe disengages the first member from the second member and releases any debris that may be clogging the strainer formed at the engaging interface between the first and second members. In a preferred embodiment, the first member includes a generally spherical valve member and the second member includes a ring having a plurality of serrations extending from the ring to engage with the first member, such that the engaging interface between the serrations and the spherical valve member forms a series of apertures or strainer perforations that permit sample fluid to pass while preventing debris entrained within the sample fluid and larger than the strainer apertures from passing beyond the second member.

The above and still further objects, features and advantages of the present invention will become apparent upon consideration of the following detailed description of a specific embodiment thereof, particularly when taken in conjunction with the accompanying drawings wherein like reference numerals in the various figures are utilized to designate like components.

DETAILED DESCRIPTION OF THE PREFERRED EMBODIMENTS

Figure 1:
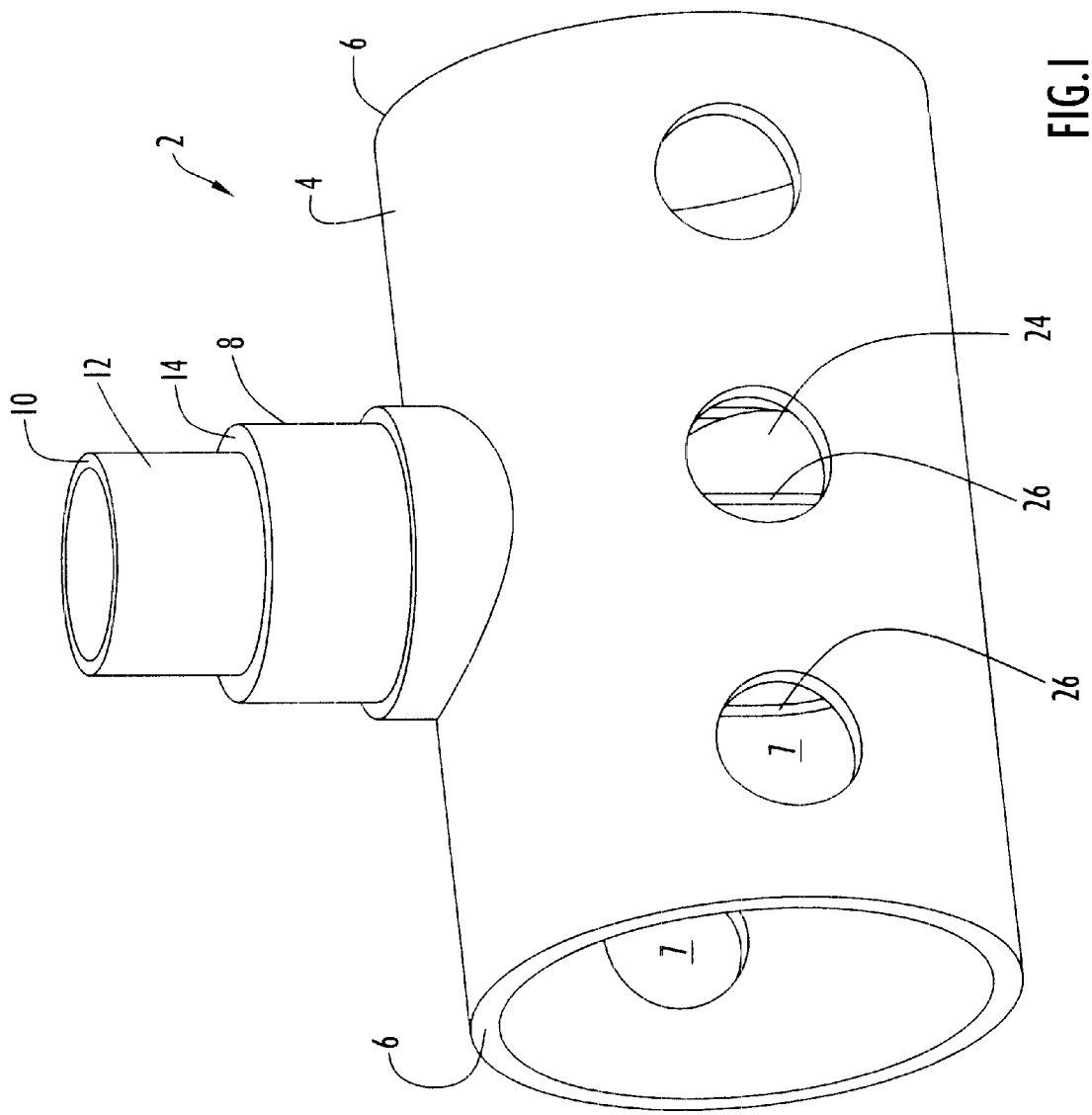
FIG. 1 is view in perspective of an exemplary embodiment of a sample probe in accordance with the present invention.
Figure 2:
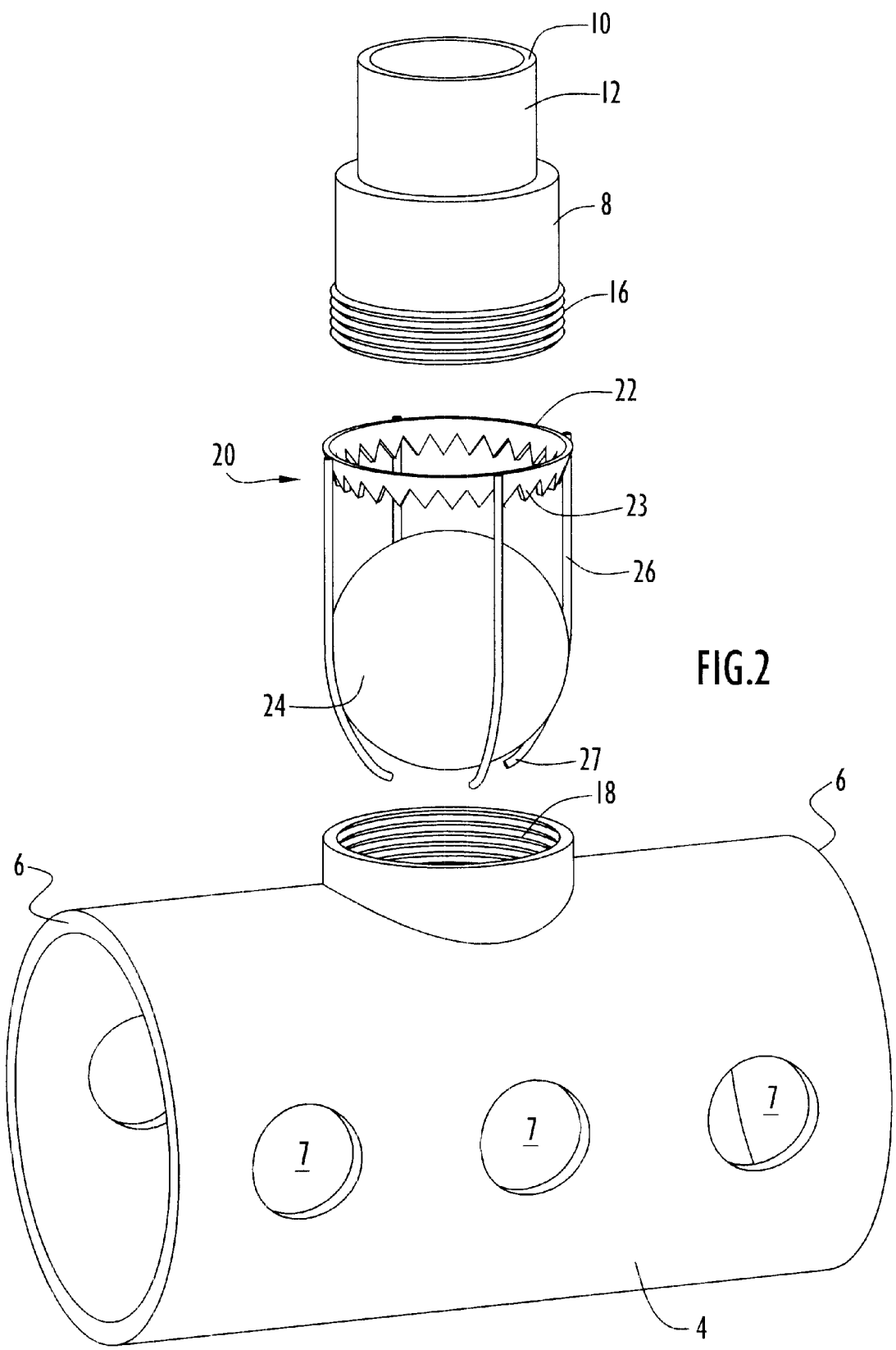
FIG. 2 is an exploded view in perspective of the sample probe of FIG. 1.

In accordance with the present invention, a sample probe is provided including a fitting that is securable to a fluid supply source to permit a fluid sample to be filtered or strained within the fitting and diverted to a fluid collector. The fluid to be sampled by the sample probe may be liquid or gaseous. Referring to FIGS. 1 and 2, a sample probe 2 includes a tee type fitting having a generally cylindrical and hollow base portion 4 and openings at its longitudinal ends 6 that serve as inlets to permit flow of fluid into the tee fitting at either end when a suitable negative pressure is applied in the fitting as described below. The base portion also includes a series of openings 7 spaced along its longitudinal surface that also provide inlets for fluid flowing within the fitting. Openings 7 further serve to strain large debris flowing within the fluid. A generally cylindrical and hollow adapter 8 extends transversely at an angle of about 90° from the base portion between longitudinal ends 6 and includes an opening at its terminal end 10 that serves as an outlet for fluid flowing from the fitting to a fluid collector (not shown). The adapter further includes a reduced-diameter section 12 extending from about the center portion of the adapter to terminal end 10. A shoulder 14 is formed at the junction between the reduced diameter section and the larger diameter section of the adaptor extending to the base portion. The reduced diameter section of the adaptor permits a flexible hose or other type of conduit to be secured to the adaptor for receiving strained fluid samples from the fitting and delivering those fluid samples to the fluid sample collector. The base portion and adapter may be constructed of any rigid material suitable for processing and handling of fluids. Preferably, the materials are constructed of a corrosion resistant material (e.g., stainless steel, polypropylene, PTFE, etc.) to prolong the longevity of the sample probe when immersed in fluids containing varying types of contaminating debris (e.g., raw sewage from a municipal waste water system).

The adapter of sample probe 2 is removably secured to the base portion of the fitting to permit easy access to a strainer assembly 20 disposed within the fitting. Referring to FIG. 2, adapter 8 includes a male threaded portion at a connecting end 16 that is secured to a female threaded tee portion 18 extending transversely from base portion 4 between longitudinal ends 6. Alternatively, the adapter may be welded or secured in any other permanent or removable manner to the base portion.

Strainer assembly 20 includes a generally spherical valve member 24 secured between a serrated ring 22 and wire members 26 extending from the ring. The valve member is suitably dimensioned to prevent complete passage of valve member 24 through the ring. Wire members 26 are connected to the ring at spaced locations around the circumference of the ring and extend in a substantially linear manner from the ring to terminate at curved ends 27. The curved ends of the wire members extend radially inward with respect to the ring to prevent the spherical member from passing beyond the curved ends. Basically, the space defined between the wire members and the ring forms a cage that retains valve member 24 therein. The dimensions of the cage, which are based upon the dimensions of the ring and wire members, are selected to permit limited movement of the valve member between the wire member curved ends and the ring. As further described below, the valve member is forced against the ring or the curved ends of the wire members depending upon the pressures applied to the fluid within the sample probe. The wire members, ring and valve member may be constructed of any suitable material, such as the materials described above for the fitting. Additionally, depending upon the types of fluid pressures generated within the sample probe for a particular application, construction of the valve member may be further selected to provide the valve member with a buoyancy that ensures contact between the valve member and the ring when fluid flows within the fitting from the base portion to the adapter.

Figure 3:
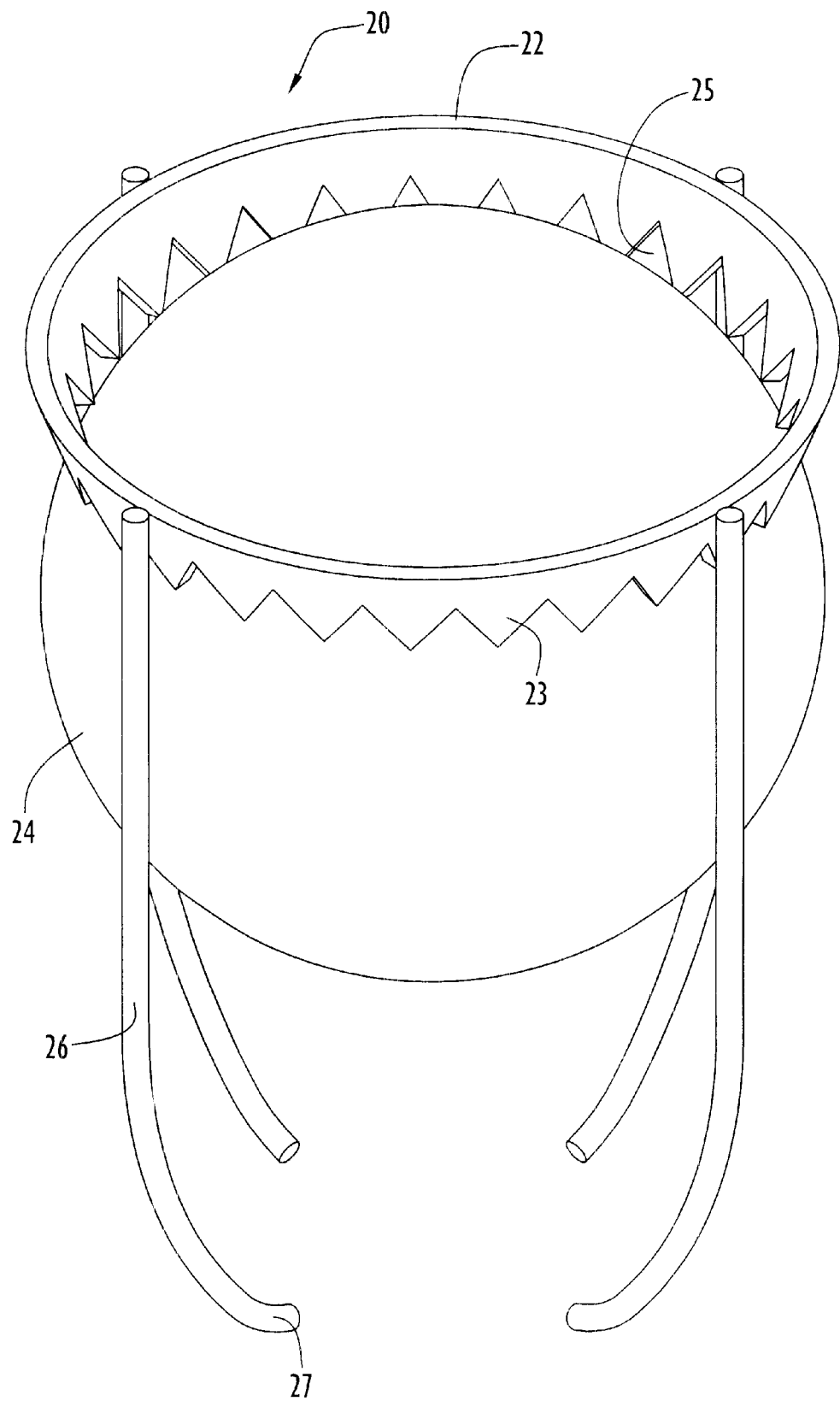
FIG. 3 is a view in perspective of the strainer assembly of FIG. 1 showing the valve member engaging the serrated ring to form a strainer.

Ring 22 includes a plurality of serrations 23 having triangular or tooth-shaped configurations and extending at spaced locations along the circumference of the ring. The serrations extend from the ring in a direction facing the valve member within the cage to provide an engaging interface with the valve member when the valve member approaches and engages the ring. An isolated view of the strainer assembly is illustrated in FIG. 3 and shows the engaging interface between the ring serrations and the valve member. As is clear from FIG. 3, ring serrations 23 slant inward from the ring toward each other such that contact between the valve member and the serrations occurs near the triangular tip of each serration. However, the serrations may extend in any suitable direction from the ring (e.g., radially in a plane defined by the ring or at an angle to a plane defined by the ring) that ensures contact of the serrations with the valve member. A series of spaced strainer apertures 25 are formed at the engaging interface between the valve member and the ring serrations. The boundary of each strainer aperture is defined between a surface of the valve member and the facing edges of two neighboring ring serrations that are adjacent that valve member surface. At the engaging interface, the valve member plugs the ring opening so that fluid flowing through the strainer assembly is forced through the strainer apertures. The strainer apertures prevent passage of debris entrained in the sample fluid that is larger than the apertures while allowing the sample fluid to pass beyond the strainer cage and into the adapter. It will be appreciated that a desired strainer aperture size is achieved by selecting appropriate dimensions for the valve member, ring and ring serrations. Thus, the selection of specific dimensions for components of the valve assembly will depend upon factors such as the required degree of straining or filtering of the sample fluid and strainer capacity for a particular application.

The strainer assembly may be secured in any suitable manner within the fitting. In the embodiment of FIGS. 1–3, strainer assembly 20 is secured within base portion 4 by securing ring 22 to an interior surface or interior extending section (e.g., a flange) of base portion 4 located at base opening 18. The ring may be permanently or releasably secured (e.g., via a weld or threaded engagement) to the base portion interior surface. Alternatively, ring 22 may be releasably or permanently secured directly to connecting end 16 of adapter 8. In instances where the ring is to be secured directly to the connecting end of the adapter, the valve assembly is preferably dimensioned to fit through the opening in the base portion to allow the adapter to be secured to the base portion while the valve assembly is secured to the adapter connecting end. When the ring is secured within the base portion, the strainer assembly is positioned within the fitting directly below and in alignment with the adapter.

The sample probe may be secured within a conduit in a variety of different ways to facilitate sampling of fluids flowing within the conduit. In an exemplary embodiment illustrated in FIGS. 4 and 5, sample probe 2 is secured within a fluid flow pipe 40 by inserting adapter 8 through an opening on the longitudinal surface of the pipe. An annular resilient sealing member 42 (e.g., a rubber gasket or bushing) is then inserted between the adapter and the longitudinal surface edges of the pipe that define the pipe opening. The sealing member firmly secures the sample probe within the pipe and also establishes a fluid tight seal at the pipe opening.

A flexible conduit 44 (e.g., a rubber hose) is secured to reduced diameter section 12 of adapter 8 with a clamp or other suitable fastener (not shown) to provide a fluid tight seal between the conduit and the adapter. The flexible conduit delivers fluid passing through the sample probe to the sample collector for further processing of the fluid sample. A suction device (e.g., a peristaltic pump) may be provided at the sample collector or at any suitable location along the flexible conduit to provide a negative pressure within the fitting so as to draw or suction a fluid sample into the fitting, through the strainer assembly and adapter and into the flexible conduit. The amount of negative pressure to be applied within the sample probe will vary based upon a number of factors, such as the size and orientation of the probe with respect to the fluid supply conduit, fluid flow capacities, the physical characteristics of the fluid to be processed, etc. The suction device is further configured to reverse fluid flow through the sample probe by applying a positive pressure within the fitting to force fluid out of the fitting and into the fluid supply source. Positive pressures are applied in situations when back flushing is desired to remove debris that may have collected on the strainer apertures.

Figure 4:
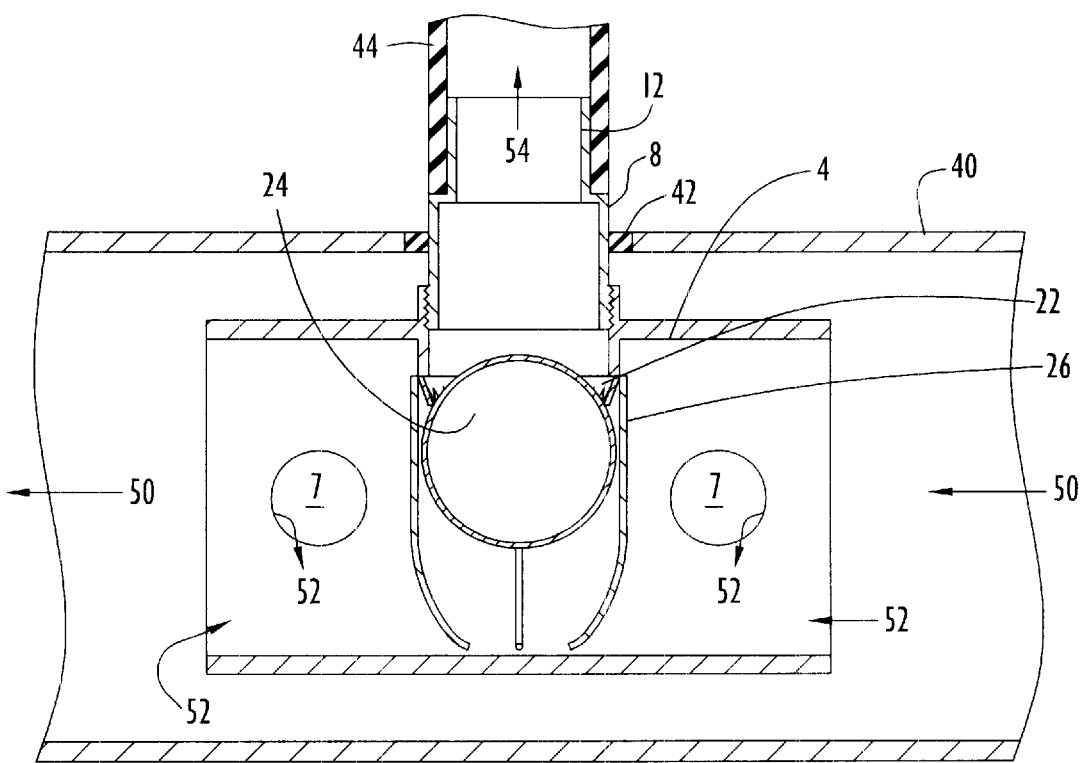
FIG. 4 is a view in section of the sample probe of FIG. 1 installed within a fluid supply conduit and in a fluid filtration operative mode.
Figure 5:
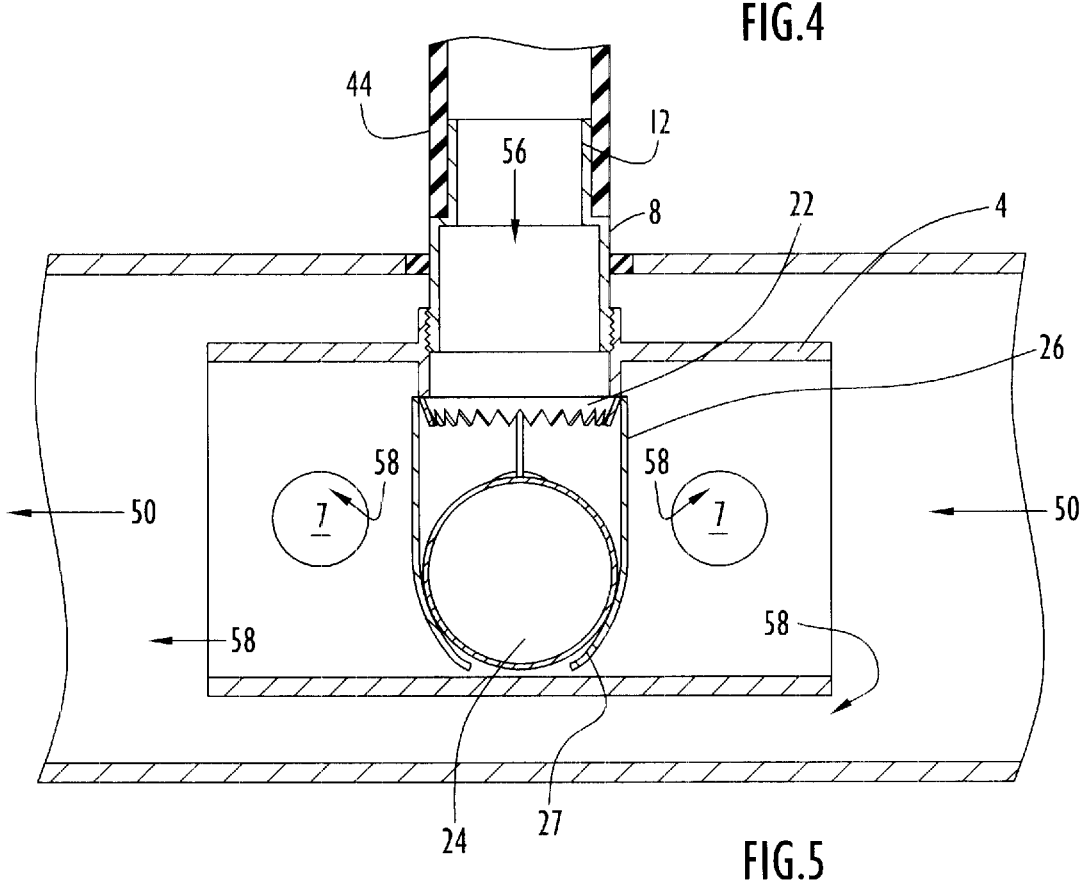
FIG. 5 is a view in perspective of the sample probe of FIG. 1 installed within a fluid supply conduit and in a back flushing operative mode.

It is noted that, in the embodiment of FIGS. 4 and 5, the sample probe is aligned substantially vertically within the fluid pipe such that fluid flows through the strainer assembly against the opposing gravitational forces acting on the fluid. However, operation of the sample probe is not limited to that vertical orientation; rather, the strainer assembly is also effective in other vertical or horizontal orientations. The selection of a specific orientation of the sample probe with respect to a fluid supply source will therefore be based upon a particular application and corresponding factors relating to that application (e.g., fluid pressures within the fitting, fluid flow capacities, physical characteristics of the sample fluid, etc.).

Operation of the sample probe is described with reference to FIGS. 4 and 5. Specifically, a fluid to be sampled flows within pipe 40 in the general direction depicted by arrows 50 in FIG. 4. The fluid may be gaseous or liquid and contains debris entrained in the fluid. A negative pressure is applied within the sample probe by a suction device that is in fluid communication with the sample probe and located downstream from the strainer assembly (e.g., at a location along the flexible conduit or at a fluid sample collector downstream of the flexible conduit). The applied negative pressure forces fluid to flow within base portion 4 at open longitudinal ends 6 as well as longitudinally spaced openings 7. The directions at which fluid enters the base portion as a result of the applied negative pressure are generally depicted by arrows 52 in FIG. 4. Openings 7 also serve as larger straining apertures to limit larger sized debris from passing through those openings into the base portion. The applied negative pressure also forces valve member, located between wire members 26, toward serrated ring 22, where it engages with serrations 23 and is prevented from passing through the ring. Engagement of the valve member with the ring serrations results in the formation of a series of strainer apertures disposed circumferentially about the ring. The strainer apertures permit sample fluid to pass through the ring and into adapter 8 while collecting and removing undesirable debris from the strained fluid. The strained fluid sample passes through the adapter (i.e., in the general direction indicated by arrow 54) and into flexible conduit 44 for delivery to the fluid sample collector.

The strainer assembly design further permits easy back flushing of the sample probe in situations where the probe may become clogged with an accumulation of strained debris. Referring to FIG. 5, the suction device is adjusted to reverse fluid flow through the probe by generating a positive pressure within the flexible fluid conduit and fitting. Fluid flow (generally indicated by arrow 56 in FIG. 5) is directed from flexible conduit 44 into adapter 8 and forces valve member 24 toward curved ends 27 of wire members 26. The wire member curved ends prevent the valve member from escaping from the cage. Any debris that may have collected along the strainer apertures formed between the ring serrations and the valve member is dislodged by fluid flowing into base portion 4 and through any of the open longitudinal ends 6 or openings 7 spaced longitudinally along the base portion (generally indicated by arrows 58 in FIG. 5). Additionally, any larger debris that may have collected at openings 7 along the longitudinal surface of the base portion will be removed by fluid forced through those openings. Dislodged debris continues to travel away from the sample probe in the direction of fluid flow in pipe 40 (generally indicated by arrow 50). Upon removal of a desired amount of debris from the strainer assembly and the openings on the longitudinal surface of the base portion, the suction device may again be adjusted to generate a desired negative pressure within the sample probe so as to provide additional strained fluid samples to the fluid sample collector.

Figure 6:
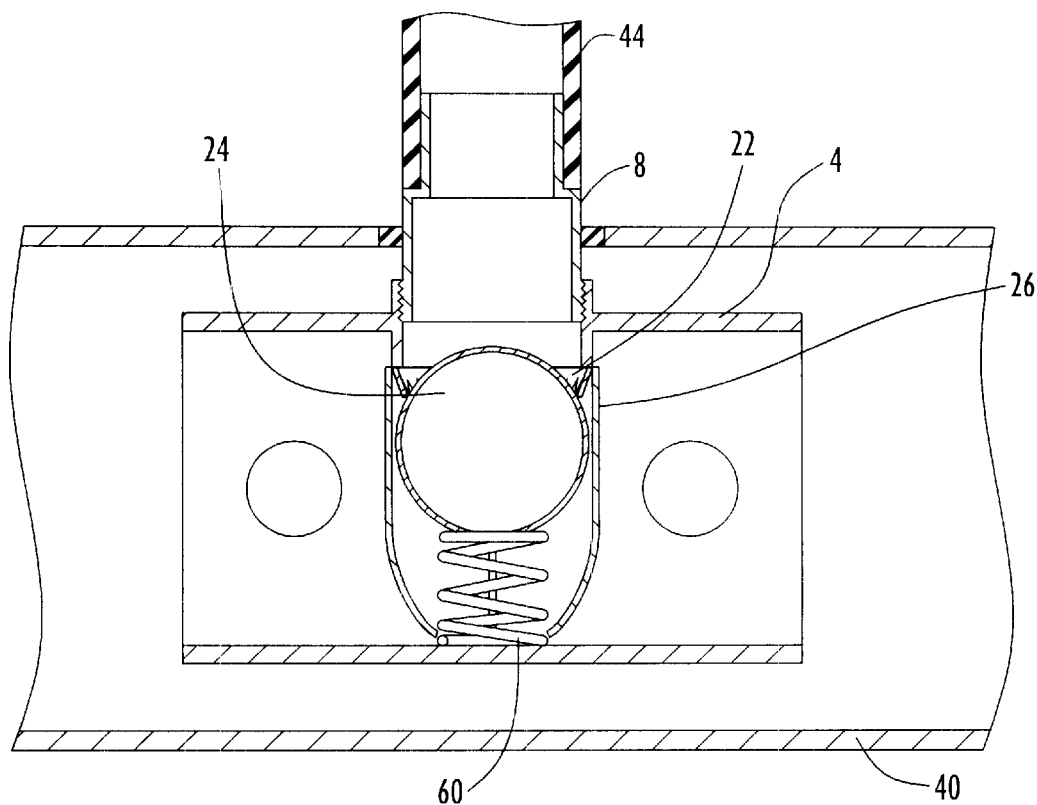
FIG. 6 is a view in section of an alternative embodiment of a sample probe in accordance with the present invention, where the sample probe is installed within a fluid supply conduit and in a fluid filtration operative mode.
Figure 7:
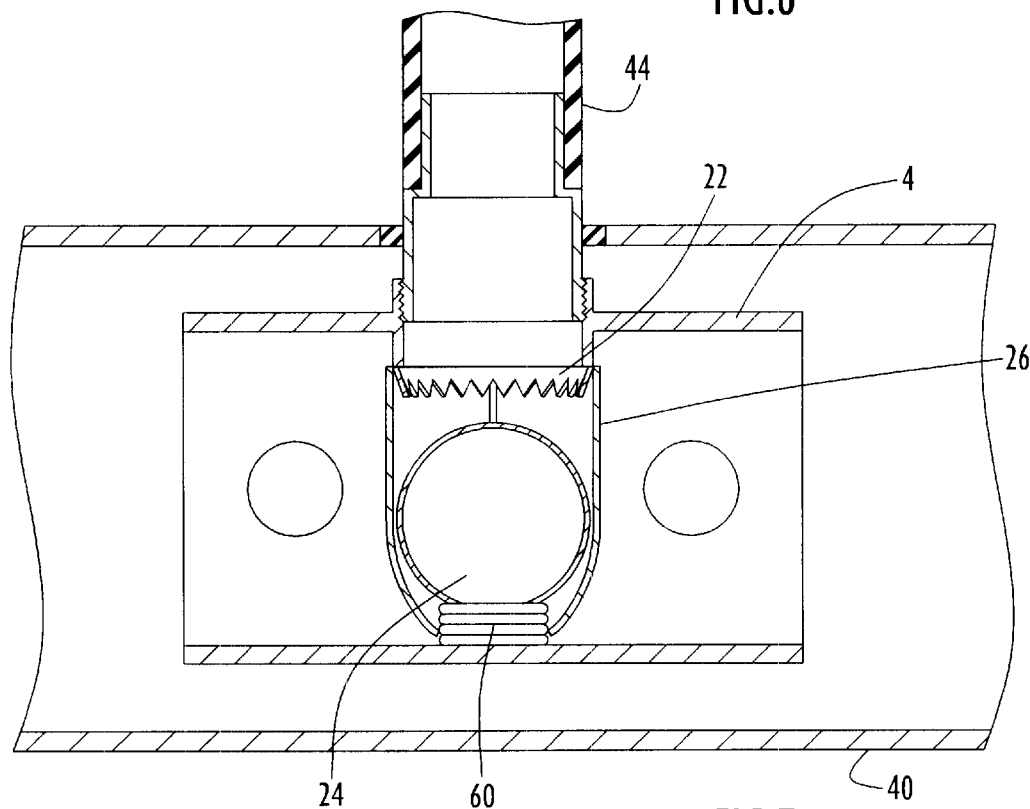
FIG. 7 is a view in section of the sample probe of FIG. 6 installed within a fluid supply conduit and in a back flushing operative mode.

In an alternative embodiment, the valve assembly of the sample probe includes a resilient biasing member to bias the valve member toward the serrated ring during sample collection procedures. Employing such a biasing member is useful, e.g., in gaseous fluid applications where the negative pressure required to draw a gaseous fluid sample from the sample probe to a collector without disrupting the overall fluid flow in the pipe is insufficient to establish an appropriate interface between the valve member and the serrated ring. Referring to FIGS. 6 and 7, valve assembly 20 of sample probe 4 is further provided with a resilient biasing member in the form of a coil spring 60. Alternatively, it is noted that the resilient biasing member may be any type of spring (e.g., a leaf spring) or other biasing device that will maintain engagement between the valve member and the serrated ring during sampling of fluid within the pipe.

Coil spring 60 is secured at one end to an interior surface of base portion 4 beneath valve member 24. The other end of the coil spring engages the valve member within the cage formed between wire members 26. The coil spring is suitably dimensioned to contact an appropriate surface area of the valve member while preventing the valve member from passing through any of the coils of the spring. Optionally, the other end of the coil spring may be secured to the valve member in any suitable manner (e.g., with adhesive). The spring bias of the coil spring maintains engagement between valve member 24 and serrated ring 22 until a suitable back flow pressure is applied to compress the spring and allow the valve member to separate from the ring.

In operation, the sample probe of FIGS. 6 and 7 operates in a substantially similar manner as the embodiment described in FIGS. 4 and 5. Coil spring 60 forces valve member 24 against the serrations 23 on ring 22 (FIG. 6) to form strainer apertures located circumferentially around the ring. A negative pressure is applied within the fitting by a suction device disposed along flexible conduit 44 or at a sample fluid collector, forcing a fluid sample to be drawn from fluid flowing in pipe 40 into base portion 4 and through the strainer apertures of ring 22. The strained fluid sample continues to travel through the adapter and into the flexible conduit for delivery to the fluid sample collector. When a back flushing procedure is necessary to remove unwanted debris from the strainer apertures of the sample probe, a positive pressure is applied that is sufficient to force the valve member against the coil spring, thus forcing the coil spring to compress (FIG. 7) and allow the valve member to separate from the ring. Any unwanted debris accumulated at the interface between the valve member and the ring is then forced out of the fitting and carried away with the general flow of fluid within pipe 40. The alignment between the valve member and the coil spring is substantially maintained during compression and expansion of the coil spring due to the limited spatial freedom allowed the valve member within the cage by the wire members.

It will be appreciated that the embodiments described above and illustrated in the drawings represent only a few of the many ways of implementing a back flushable sample probe for collecting and straining fluid samples from a fluid supply line in accordance with the present invention. For example, the sample probe may include fittings of varying types other than tee type fittings, such as wye type fittings, cross type fittings or any other type of fitting that enables the diverting of a fluid sample from a main fluid flow line. Alternatively, the sample probe may employ, e.g., a coupling or other similar type fitting with the valve assembly disposed therein, where the sample probe is disposed along a diverter line that connects the fluid supply line with the sample collector. The sample probe may be partially or completely disposed within the fluid supply line and may be secured to the fluid supply line in any suitable manner. Alternatively, the sample probe may be secured at its longitudinal ends to portions of a fluid supply line. In situations where the sample probe is not secured within a fluid supply line, the openings spaced longitudinally along the sample probe fitting would be sealed or eliminated.

The strainer assembly may be disposed at any suitable location within the main body portion of the fitting. Alternatively, the strainer assembly may be disposed within the adapter portion of the fitting. The valve member and serrations on the ring of the sample probe strainer assembly may be of any suitable dimensions and configurations to facilitate the formation of strainer apertures of any suitable size upon engagement between the valve member and ring. The size of the valve member and serrations can be of any selected sizes or configurations to optimize performance in terms of flow rate, velocity and straining characteristics. It is conceivable that modular assembly could enable the user to modify the strainer performance to suit needs of particular media. Further, the geometric shape of the serrations on the ring are not limited to triangular configurations; rather, the serrations could be rounded, squared, or have any other suitable geometric configuration to ease back-flushing, limit entrapment of material and affect the flow profile through the device. Alternatively, the ring may be provided without serrations, and the valve member may be provided with grooves or indentations or may have a selected multi-surfaced geometry to facilitate the formation of strainer apertures upon contact between the ring and valve member. Additionally, although the ring described in the previous embodiments is secured within the fitting, the ring may alternatively be coupled in any suitable manner within the fitting to allow the ring to movably engage and disengage with the valve member within the fitting. The cage which houses the valve member may have any suitable dimensions and configurations to prevent the valve member from escaping the cage while simultaneously permitting the flow of fluid through the cage.

Having described preferred embodiments of a back flushable sample probe, variations and changes will be suggested to those skilled in the art in view of the teachings set forth herein. It is therefore to be understood that all such variations, modifications and changes are believed to fall within the scope of the present invention as defined by the appended claims.

What is claimed:

1. A back flushable sample probe for straining a fluid sample from a fluid supply source, comprising:
    a hollow fitting including an inlet to receive the fluid sample from the fluid supply source and an outlet to expel the fluid sample from the fitting; and
    a strainer assembly disposed within the fitting between the fitting inlet and the fitting outlet, the strainer assembly comprising a first member movable within the fitting and a second member disposed within the fitting and coupled to the fitting, the first member being movable toward the second member to contact the second member and form a strainer at an engaging interface between the first and second members, wherein the strainer removes debris from the fluid sample when the fluid sample travels within the fitting from the fitting inlet to the fitting outlet.

2. The sample probe of claim 1, wherein the first member is further movable away from the second member when the sample fluid is back flushed from the fitting outlet toward the fitting inlet.

3. The sample probe of claim 1, wherein the strainer formed at the engaging interface between the first and second members includes a plurality of apertures defined between surface portions of the first member and surface portions of the second member.

4. The sample probe of claim 3, wherein the first member comprises a spherical valve, the second member comprises a ring including a plurality of serrations extending from the ring to contact the spherical valve when the spherical valve engages the ring, and the apertures are defined between facing edges of neighboring serrations and adjacent surface portions of the spherical valve.

5. The sample probe of claim 4, wherein the strainer assembly further includes a cage that surrounds the spherical valve and limits movement of the spherical valve with respect to the ring.

6. The sample probe of claim 5, wherein the cage comprises a plurality of wire members extending at circumferentially spaced locations from the ring and terminating in ends curving radially inward with respect to the ring to prevent the spherical valve from escaping from the cage.

7. The sample probe of claim 1, wherein the fitting includes a main body and an adapter extending transversely from the main body, the fitting inlet is disposed on the main body and the fitting outlet is disposed on the adapter.

8. The sample probe of claim 7, wherein the sample probe is immersable within the fluid supply source, and the main body includes a plurality of apertures disposed along a longitudinal surface of the main body.

9. The sample probe of claim 1, wherein the strainer assembly further includes a biasing member that resiliently biases the first member against the second member.

10. A strainer comprising:
    a hollow fitting including an inlet to receive fluid into the fitting and an outlet to expel strained fluid from the fitting;
    a first member movable within the fitting;
    a second member disposed within the fitting and coupled to the fitting; and
    a cage comprising a plurality of wire members extending at spaced locations from the second member to surround and prevent the first member from escaping from the cage;
    wherein the first member is movable toward the second member to form a plurality of strainer apertures upon the first member engaging with the second member, the strainer apertures being defined between surface portions of the first member and adjacent surface portions of the second member.

11. The strainer of claim 10, wherein the first member comprises a spherical valve, the second member comprises a ring including a plurality of serrations extending from the ring to contact the spherical valve when the spherical valve engages the ring, and the strainer apertures are defined between facing edges of neighboring serrations and adjacent surface portions of the spherical valve.

12. In a fluid sampling system including a fluid supply source, a sample probe in fluid communication with the fluid supply source, the sample probe including a hollow fitting and a strainer assembly disposed within the fitting, and a fluid collection conduit in fluid communication with the sample probe, a method of straining a fluid sample for subsequent analysis, the method comprising:

(a) applying a negative pressure within the sample probe to force a fluid sample from the fluid supply source to enter an inlet of the fitting and travel toward an outlet of the fitting;

(b) engaging a first member of the strainer assembly with a second member of the strainer assembly to form a strainer at an engaging interface between the first and second members;

(c) straining the fluid sample by forcing the fluid sample, via the applied negative pressure, through the strainer and collecting debris entrained within the fluid sample at the strainer; and (d) forcing the strained fluid sample, via the applied negative pressure, through the fitting outlet and into the fluid collection conduit.

13. The method of claim 12, further comprising:

(e) applying a positive pressure within the sample probe to force the fluid sample to travel from the fitting outlet to the fitting inlet and into the fluid supply source; and (f) disengaging the first member, via the applied positive pressure, from the second member to release debris collected by the strainer at the engaging interface between the first and second members and force the debris to travel within the fluid sample through the fitting inlet and into the fluid supply source.

14. The method of claim 12, wherein the strainer formed at the engaging interface between the first and second members includes a plurality of apertures defined between first surface portions of the first member and second surface portions of the second member.

15. The method of claim 12, wherein the first member comprises a spherical valve, the second member comprises a ring including a plurality of serrations extending from the ring, (b) includes:

(b.1) engaging the spherical member with the serrations of the ring to form a plurality of apertures defined between facing edges of neighboring serrations and adjacent surface portions of the spherical valve; and (c) includes:

(c.1) forcing the fluid sample through the apertures and collecting debris entrained in the fluid sample at the apertures.

16. The method of claim 12, further comprising:

(e) immersing the sample probe within the fluid supply source.

17. A back flushable sample probe for straining a fluid sample from a fluid supply source, comprising:

a means for straining the fluid sample including a first member movable with respect to a second member, wherein the first member and the second member are engageable to form a strainer for straining the fluid sample flowing between the first and second member; and a means for housing the means for straining, the means for housing including an inlet for receiving the fluid sample and an outlet for expelling fluid strained by the means for straining from the means for housing.

18. A fluid straining and sampling collection system, comprising:

a hollow fitting in fluid communication with a fluid supply source and including an inlet to receive a fluid sample from the fluid supply source and an outlet to expel the fluid sample from the fitting;

a strainer assembly disposed within the fitting between the fitting inlet and the fitting outlet, the strainer assembly comprising a first member movable within the fitting and a second member disposed within the fitting and coupled to the fitting, the first member being movable toward the second member to contact the second member and form a strainer at an engaging interface between the first and second members, wherein the strainer removes debris from the fluid sample when the fluid sample travels within the fitting from the fitting inlet to the fitting outlet;

a conduit secured to the fitting outlet to receive strained fluid expelled from the fitting outlet;

a fluid sample collector to receive the strained fluid from the conduit; and a suction device to generate a selected pressure within the conduit and the fitting so as to draw the fluid sample into the collector.

19. The collection system of claim 18, wherein the first member is further movable away from the second member when the sample fluid is back flushed from the fitting outlet toward the fitting inlet.

20. The collection system of claim 18, wherein the strainer formed at the engaging interface between the first and second members includes a plurality of apertures defined between surface portions of the first member and surface portions of the second member.

21. The collection system of claim 20, wherein the first member comprises a spherical valve, the second member comprises a ring including a plurality of serrations extending from the ring to contact the spherical valve when the spherical valve engages the ring, and the apertures are defined between facing edges of neighboring serrations and adjacent surface portions of the spherical valve.

22. The collection system of claim 21, wherein the strainer assembly further includes a cage that surrounds the spherical valve and limits movement of the spherical valve with respect to the ring.

23. The collection system of claim 22, wherein the cage comprises a plurality of wire members extending at circumferentially spaced locations from the ring and terminating in ends curving radially inward with respect to the ring to prevent the spherical valve from escaping from the cage.

24. The collection system of claim 18, wherein the fitting includes a main body and an adapter extending transversely from the main body, the fitting inlet is disposed on the main body, the fitting outlet is disposed on the adapter and the conduit is secured to the adapter.

25. The collection system of claim 24, wherein the sample probe is secured within the fluid supply source with the adapter extending from an opening in the fluid supply source, and a longitudinal surface of the main body includes a plurality of apertures to receive a portion of the fluid sample entering the main body.

26. The collection system of claim 18, wherein the strainer assembly further includes a biasing member that resiliently biases the first member against the second member.

* * * * *